United States Patent
Bougamont et al.

(10) Patent No.: US 6,234,365 B1
(45) Date of Patent: May 22, 2001

(54) SPRAYER NOZZLE WITH CLOSING MEMBRANE

(75) Inventors: Jean-Louis Bougamont; Pascal Hennemann, both of Eu; David Leuliet, Mers les Bains, all of (FR)

(73) Assignee: Rexam Sofab, Le Treport (FR)

( * ) Notice: Subject to any disclaimer, the term of this patent is extended or adjusted under 35 U.S.C. 154(b) by 0 days.

(21) Appl. No.: 09/554,091
(22) PCT Filed: Nov. 25, 1998
(86) PCT No.: PCT/FR98/02520
§ 371 Date: Jul. 21, 2000
§ 102(e) Date: Jul. 21, 2000
(87) PCT Pub. No.: WO99/26688
PCT Pub. Date: Jun. 3, 1999

(30) Foreign Application Priority Data

Nov. 25, 1997 (FR) .................................................. 97 14762

(51) Int. Cl.⁷ ....................................................... B65D 5/72
(52) U.S. Cl. .................... 222/494; 222/490; 222/189.06; 222/189.09; 222/189.11; 222/321.6; 222/380; 222/402.12; 239/533.13; 239/570; 239/571; 239/575; 239/583; 239/602
(58) Field of Search ......................... 222/189.06, 189.09, 222/189.11, 321.6, 380, 402.12, 494, 490; 239/533.13, 602, 570, 571, 583, 575

(56) References Cited

U.S. PATENT DOCUMENTS

| | | | |
|---|---|---|---|
| 5,154,325 | * 10/1992 | Ryder et al. | 222/189 |
| 5,181,658 | * 1/1993 | Behar | 239/493 |
| 5,195,665 | * 3/1993 | Lina | 222/496 |
| 5,203,840 | * 4/1993 | Graf et al. | 222/321 |
| 5,238,153 | * 8/1993 | Castillo et al. | 222/189 |
| 5,257,726 | * 11/1993 | Graf et al. | 222/320 |
| 5,377,880 | * 1/1995 | Moretti | 222/207 |
| 5,829,645 | * 11/1998 | Hennemann | 222/189.09 |
| 5,988,449 | * 11/1999 | Fuchs et al. | 222/189.11 |

* cited by examiner

Primary Examiner—Kevin Shaver
Assistant Examiner—Frederick C Nicolas
(74) Attorney, Agent, or Firm—Bacon & Thomas, PLLC

(57) ABSTRACT

The invention relates to an endpiece for dispensing and/or measuring out liquid pharmaceutical substances, the endpiece comprising a cylindro-conical body (1) fitted with a bottom base (13) for receiving thrust and for coupling to a tank capable of being put under pressure, and an axial ejection duct (10) containing a central core (2) and communicating firstly at its top end with a spray nozzle, and secondly at its bottom end with the tank, it is characterized in that the top end of the ejection duct (10) is closed in temporary and leakproof manner by a wall (111) which is secured to the top portion (1a) of the body (1) and which extends perpendicularly to the duct, the wall being movable in reversible manner under drive from the substance, said wall being provided with a central orifice (110) capable of being closed in the closed position by a stud (20) secured to the core (2) being forced thereagainst, the periphery of the wall being attached to said body (1) via an elastically deformable link element (112) enabling the wall (111) to move in axial translation under pressure.

13 Claims, 4 Drawing Sheets

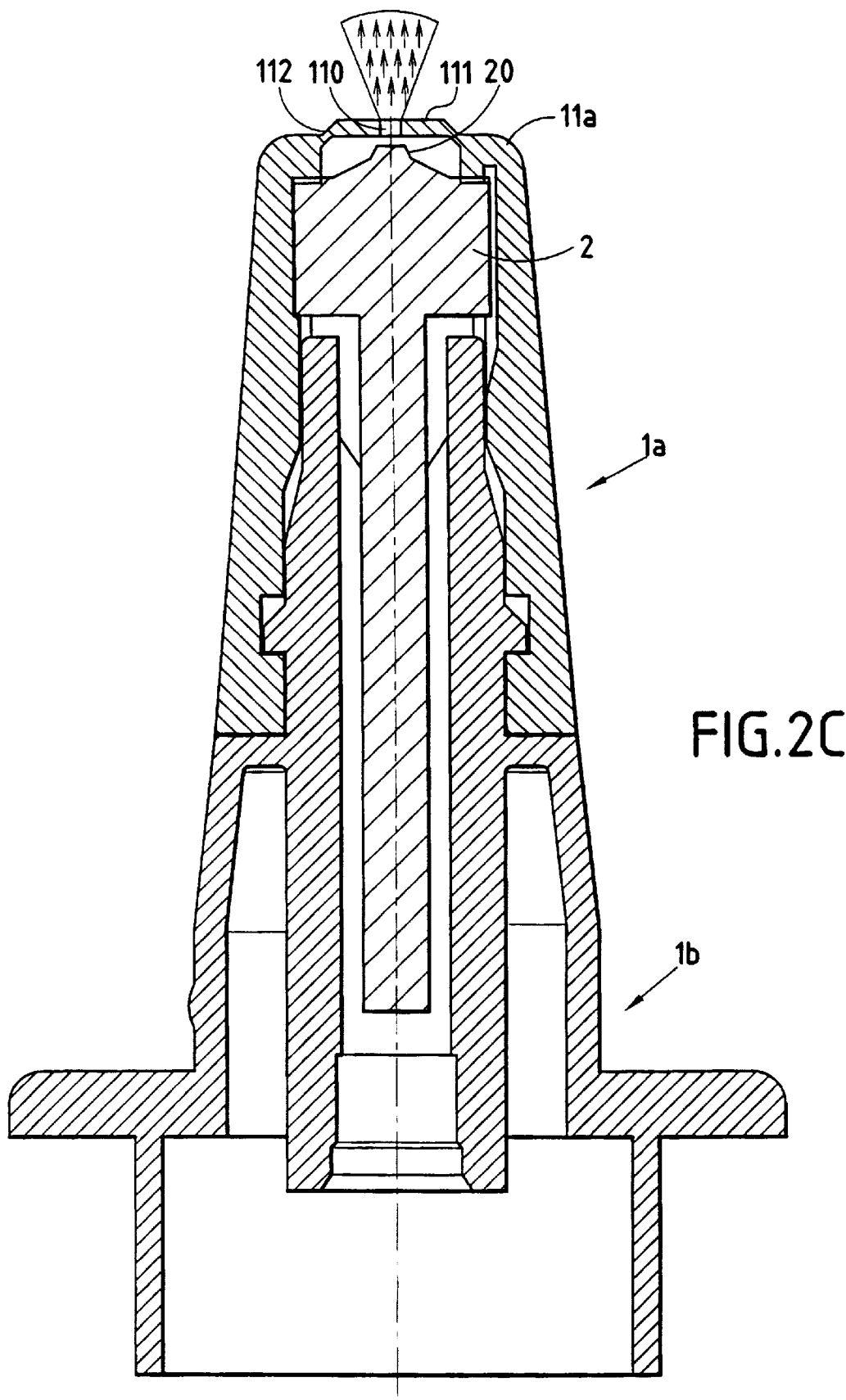

SPRAYER NOZZLE WITH CLOSING MEMBRANE

Figure 1:
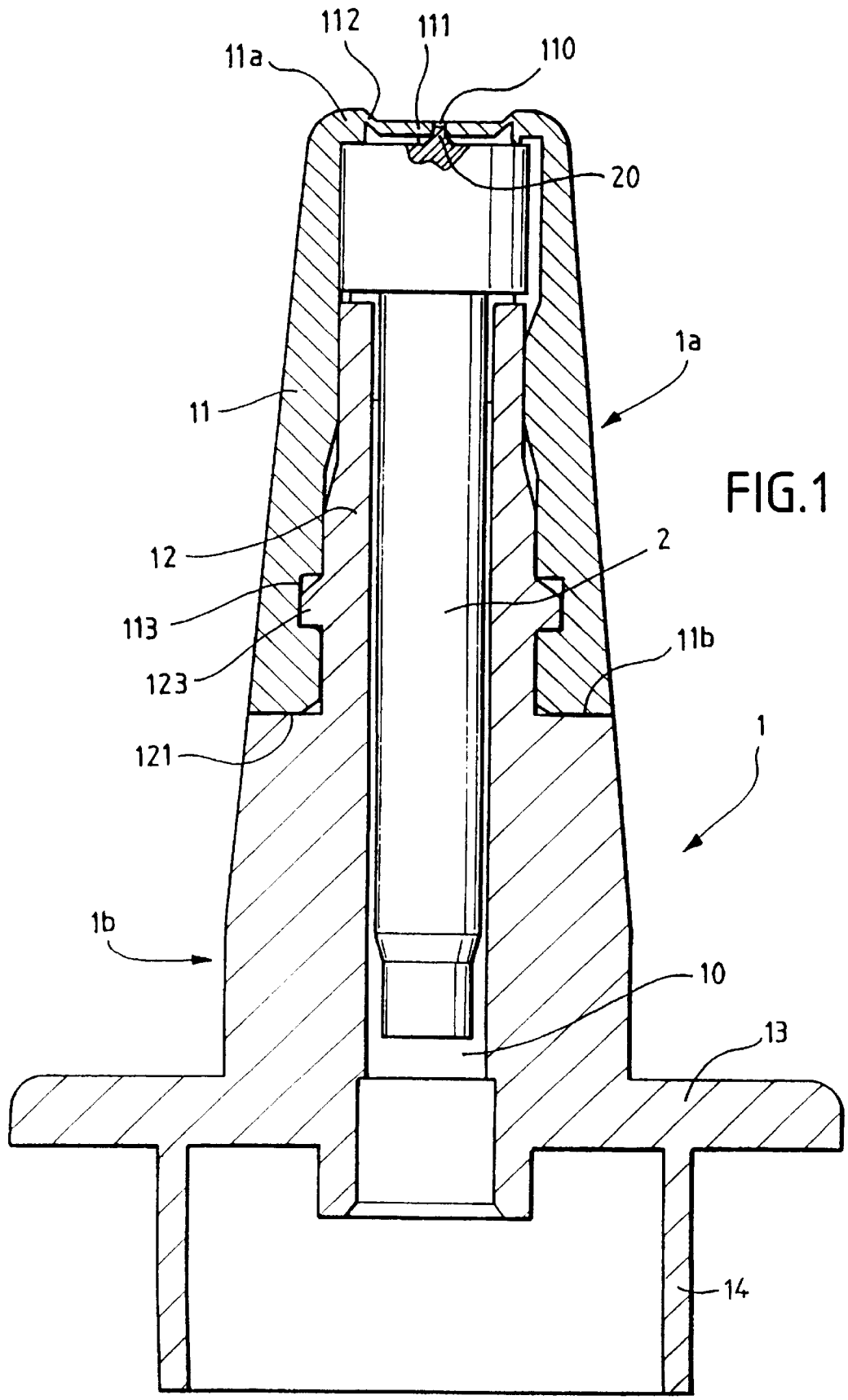

The present invention relates to an endpiece for dispensing liquid pharmaceutical substances.

Traditional endpieces, such as those for nasal application, generally comprise a cylindro-conical body designed to be mounted via a coupling base on a tank that can be put under pressure.

An axial ejection duct containing a central core is formed inside the body and it communicates firstly at its top end with a spray valve or nozzle, and secondly at its bottom end with the tank via means for pressurizing and/or measuring out the substance.

Such endpieces are described, for example, in WO 94/29187 in which the ejection duct is closed by a wall that has a central orifice co-operating in leakproof manner with a stud and connected to the endpiece by deformable link elements enabling it to move axially.

However, with said endpieces, the substance is not provided with bacteriological protection in reliable manner.

The spray valve or nozzle does not, on its own, constitute a mechanical barrier that is sufficiently effective to limit in significant manner, or a fortiori to eliminate, any risk of the substance becoming contaminated.

Although protection can be improved by incorporating antibacterial agents or bactericides in the material from which endpieces are made, the search for a fully satisfactory solution further includes, above all, developing mechanical means capable of providing a high level of mechanical isolation for the ejection duct so as to obtain better confinement of the substance inside the tank.

Furthermore, when operation of the pressurization means requires pressures to be brought back into equilibrium between the tank and the outside, the air intake must not constitute a source of pollution or deterioration of the substance, and it must compromise neither the sealing of the endpiece nor the quality of dispensing or dose-measurement.

Finally, in general, conventional endpieces are not suitable for being sterilized by all methods of sterilization.

An object of the present invention is to resolve those technical problems in satisfactory manner.

According to the invention, this object is achieved by means of an endpiece for dispensing and/or measuring out liquid pharmaceutical substances, the endpiece comprising a cylindro-conical body fitted with a bottom base for receiving thrust and for coupling to a tank capable of being put under pressure, and an axial ejection duct containing a central core and communicating firstly at its top end with a spray nozzle, and secondly at its bottom end with the tank, the endpiece being characterized in that the top end of the ejection duct is closed in temporary and leakproof manner by a wall which is secured to the top portion of said body and which extends perpendicularly to said duct, the wall being movable in reversible manner under drive from the substance, said wall being provided with a central orifice capable of being closed in the closed position by a stud secured to the core being forced thereagainst, the periphery of said wall being attached to said body via an elastically deformable link element enabling said wall to move in axial translation under pressure.

In a particular embodiment, the top portion of said body is formed by an independent cap carrying said wall and fitted in leakproof manner to the top of a coaxial sleeve secured to the bottom portion of said body and defining at least part of the top portion of the ejection duct.

In a variant, said wall is made as a single piece together with the cap out of an elastomer material or out of an elastomer-and-thermoplastic material.

In a particular variant, said cap is locked onto said sleeve by means of snap-fastening members.

Preferably, said sleeve is connected to the bottom portion of said body via a transverse shoulder forming an abutment for the bottom edge of said cap.

In another embodiment, the top and bottom portions of said body are formed as a single piece by dual injection of an elastomer-and-thermoplastic material and of a thermoplastic material.

In another variant, said spray nozzle is formed beneath said wall by intermediate spaces situated radially outside the periphery of said wall between the inner faces of the top portion of said body and the outer envelope of said core.

According to an advantageous characteristic, said core possesses an enlarged head that is substantially cylindrical.

In another variant, the central orifice of said wall is formed by a cylindrical bore, while said stud is substantially frustoconical in profile.

Preferably, the outside face of said wall is set back from the top rim of said body so as to define a cup.

In yet another variant, the bottom base is extended downwards by a skirt designed to be engaged with radial clamping in the neck of the tank.

In yet another embodiment, more particularly applicable to an atmospheric method of dispensing, said wall is made in the form of a membrane having permeability that enables air to filter through it.

Preferably, said wall is made of silicone.

In a particular variant, said core in the closed position defines a prestressed state of the link element.

The endpiece of the invention provides reinforced sealing for the ejection duct, thereby preventing any penetration of bacteria or other biological contaminants when it is in the closed position.

Under such circumstances, and also using a bactericidal agent acting merely by contact with the substance and without migration into the substance, it is possible, after the movable wall has returned to the closed position, to perform in situ antiseptic treatment of the fraction of the substance that remains confined inside the nozzle and in the ejection duct.

Similarly, this antiseptic treatment also applies to the outside surfaces of the endpiece which are the most exposed to contaminating media.

Given the absence of any dead volume at the moving wall and the very small volumes of the intermediate spaces inside the endpiece, the efficiency of the bactericidal agent is excellent and leads to germs being rendered completely harmless.

When the pressurization means used operate with air intake, the volume of air that is sucked in is filtered through the movable wall, thereby eliminating any risk of pollution and/or of contamination.

In addition, the endpiece as a whole can be sterilized by any means, for example beta and gamma ionizing radiation, and heat treatment at temperatures of at least 120° C.

Furthermore, spraying is of very good quality, and this continues in constant and durable manner, because the wall as a whole moves uniformly in axial translation without any interfering shifts or deformation.

The endpiece of the invention can be used advantageously for dispensing and measuring out pharmaceutical substances for ophthalmological or nasal (ENT) application.

Figure 2A:
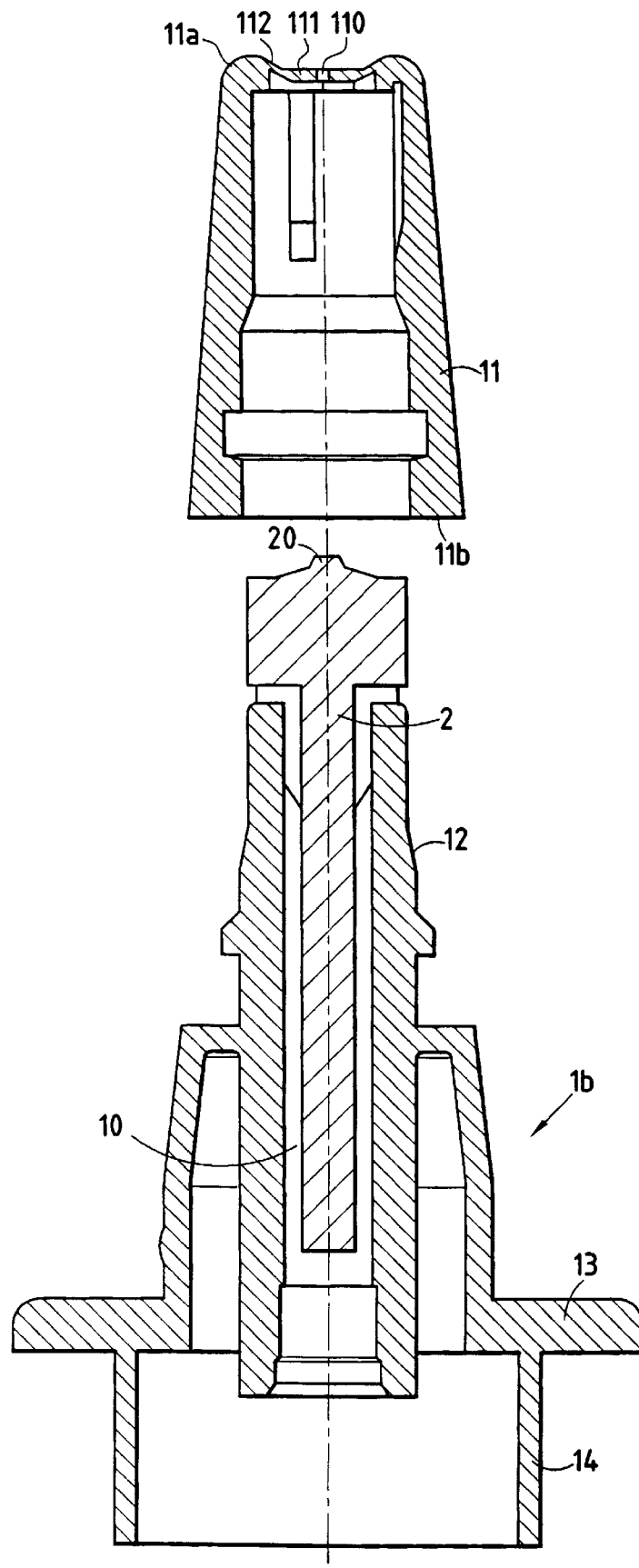
Figure 2B:
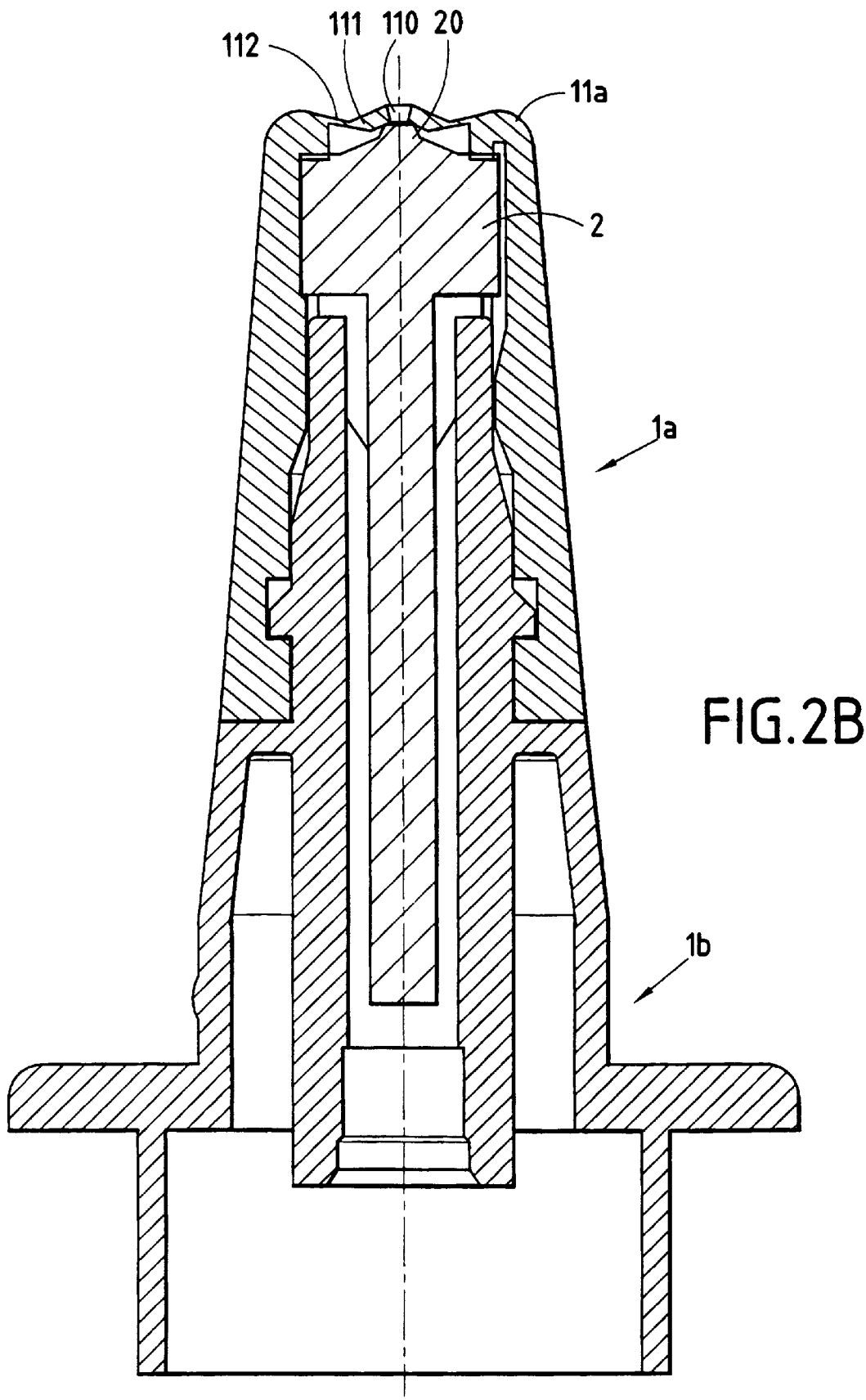

The invention will be better understood on reading the following description and the accompanying drawings, in which:

FIG. 1 is a fragmentary section view of an embodiment of the endpiece of the invention; and FIGS. 2a, 2b, and 2c are fragmentary section views of an embodiment of the endpiece of the invention, respectively in the free state, then in the assembled state in the closed position, and then in the open position.

The endpiece shown in FIG. 1 is designed to dispensed measured quantities ("doses") of a liquid pharmaceutical substance used in particular for treating diseases of the respiratory tract, or for ophthalmological treatments.

The endpiece comprises a cylindro-conical body 1 provided with a bottom base 13 for receiving manual pressure and for coupling to a tank (not shown). The bottom base 13 is itself extended downwards by a skirt 14 designed to be engaged with radial clamping in the cylindrical neck of a tank.

An axial ejection duct 10 containing a central core 2 is provided in the body 1. The core 2 is in the form of a solid and independent cylindrical piece having an enlarged head.

In a variant, the body 1 and the core can be made as a single piece.

The ejection duct 10 communicates firstly at its top end with a spray nozzle, and secondly at its bottom end with the tank, via pressurizing and/or measuring means (not shown in FIG. 1).

The top end of the ejection duct 10 is closed in temporary and leakproof manner by a transverse wall 111. The wall 111 is reversibly movable under drive from the liquid substance ejected under pressure.

The wall 111 is provided with a central orifice 110 formed by a central bore closed in the closed position by a stud 20 of substantially frustoconical profile secured to the core 2.

In the embodiment of FIG. 1, the stud 20 is received in the bore 110, whereas in the embodiment of FIG. 2a to 2c, the stud 20 presses with force against the inside face of the wall 111, bearing against the wall around the bore 110.

The spray nozzle is preferably of the "micromist" type (SOFAB terminology), being formed beneath the wall 111 by intermediate spaces extending between the inside faces of the top portion 1a of the body 1 and the outer envelope of the core 2.

The wall 111 extends perpendicularly to the axis of the duct 10 and is secured to the top portion 1a of the body 1.

The wall 111 is connected to the body 1 peripherally by means of an elastically deformable link element 112 which is preferably made in the form of an annular web.

The thickness of the link element 112 is thinner than that of the wall 111 which is therefore the more rigid.

Liquid pressure lying in the range 0.1 bars to 10 bars and generated by applying manual thrust to the base 13 (and actuating the pressurizing means) is applied against the inside face of the wall 111, and forces the link element 112 to deform elastically so as to form a hinge for the wall 111.

The wall 111 then moves upwards in axial translation remaining in planes that are substantially parallel, and releasing the orifice 110 from the stud 20 (see FIG. 2c). When the liquid pressure drops, the link element 112 exerts a return force on the wall 111 urging it towards the rest position which corresponds to the orifice 110 being closed in leakproof manner.

In the closed position of the embodiment of FIG. 1 or else.

In the free state, in the variant of FIG. 2a, the plane of the outside face of the wall 111 is set back from the top curvilinear rim 11a of the body 1 so as to define a cup.

This disposition implies that the link element 112 slopes towards the axis of the duct 10 downwards at an angle lying in the range 0 to 600°, while the side face of the wall 111 is chamfered, extending in line with the link element 112.

In a variant shown in FIG. 2b, in the assembled position, and in the position where the endpiece is closed, the stud 20 is forced against the wall 111, thereby guaranteeing that the duct 10 is closed hermetically, and also causing the wall 111 to be moved outwards a little.

In this variant, in the closed position, the link element 112 is thus deformed and remains under stress, while the cylindrical profile of the bore 110 becomes perceptibly frustoconical.

Naturally, controlling the deformation of the link element 112 involves an appropriate selection for the geometrical characteristics and the modulus of elasticity thereof.

Thus, the pressure at which the duct 10 opens depends on the area of the inside face of the wall 111 against which the liquid pressure acts, and on the return force exerted by the link element 112 that needs to be overcome in order to release the orifice 110. Overall, starting from the free state (FIG. 2a) and going to the open position of the assembled state (FIG. 2c), the wall 111 is indeed subjected to axial translation, passing via a prestressed state.

In addition, the operating conditions for the channels and the swirling array of the spray nozzle are not disturbed by the wall 111 moving since they are disposed radially on the outside of the periphery of the link element 112.

In the particular embodiment shown, the top portion 1a of the body 1 is formed by a cap 11 that is independent and whose top edge 11a carries the wall 111. The cap 11 is fitted in leakproof manner on a coaxial sleeve 12 that is secured to the bottom portion 1b of the body 1. The sleeve 12 defines at least a part of the top portion of the ejection duct 10.

The wall 111 is then made integrally with the cap 11 out of an elastomer material such as ethylene-propylenediene-monomer (EPDM) or an elastomer and thermoplastic mixture such as a mixture of polypropylene and EPDM.

In a variant embodiment, the wall 111 is implemented in the form of a membrane of permeability that is determined in such a manner as to allow incoming air to filter through so as to avoid air intake leading to any pollution or contamination of the substance (in particular any bacterial contamination).

The material used for making the membrane is preferably silicone or a silicone elastomer compound.

The permeability to air of the cap 11 made by molding a silicone elastomer lies in the range 70 microliters ($\mu$l) per 24 hours (h) to 800 $\mu$l/24 h.

The cap, which is optionally removable, is clamped radially onto the top portion of the sleeve 12 and is locked thereon via its bottom portion, e.g. by means of complementary snap-fastening members 113, 123.

The bottom portion 1b of the body 1 is preferably made of polypropylene or any other material suitable for withstanding heat treatment for sterilization.

The sleeve 12 is connected to the bottom portion 2b of the body 1 via a transverse shoulder 121 forming an abutment for the bottom edge 11b of the cap.

In another embodiment (not shown), the top and bottom portions 1a and 1b of the body 1 are implemented as a single piece by dual injection in a mold of an elastomer material and of a thermoplastic material.

Preferably, all of the zones and components of the endpiece are made using materials in which an antiseptic agent (bactericide or antibacterial agent) is incorporated, e.g. an agent based on silver ions.

What is claimed is:

1. An endpiece for dispensing and/or measuring out liquid pharmaceutical substances, the endpiece comprising a cylindro-conical body (1) fitted with a base (13) for receiving thrust and for coupling to a tank capable of being put under pressure, and an axial ejection duct (10) containing a central core (2) and communicating at a first end with a spray nozzle, and at its other end with the tank, the ejection duct (10) being closed in temporary and leakproof manner by a wall (111) which is secured to said body (1) and which extends perpendicularly to said duct, said wall being further provided with a central orifice (110) capable of being closed in the closed position by a stud (20) secured to the core (2) being forced thereagainst, the periphery of said wall being attached to said body (1) via an elastically deformable link element (112) enabling said wall (111) to move in axial translation under pressure, the endpiece being characterized in that said wall (111) is made in the form of a membrane having permeability that enables air to filter through it.

2. An endpiece according to claim 1, characterized in that the top portion (1a) of said body (1) is formed by an independent cap (11) carrying said wall (111) and fitted in leakproof manner to the top of a coaxial sleeve (12) secured to said body and defining at least part of the top portion of the ejection duct (10).

3. An endpiece according to claim 1, characterized in that the base (13) is extended downwards by a skirt (14) designed to be engaged in the tank.

4. An endpiece according to claim 1, characterized in that said wall is made of silicone.

5. An endpiece according to claim 1, characterized in that said core (2) in the closed position defines a prestressed state of the link element (112).

6. An endpiece according to claim 2, characterized in that said wall (111) is made as a single piece together with the cap (11) out of an elastomer material or out of an elastomer-and-thermoplastic material.

7. An endpiece according to claim 2, characterized in that said cap (11) is locked onto said sleeve (12) by means of snap-fastening members (113, 123).

8. An endpiece according to claims 2, characterized in that said sleeve (12) is connected to said body (1) via a transverse shoulder (121) forming an abutment for the bottom edge of said cap (11).

9. An endpiece according to claim 1, characterized in that said body (1) is formed as a single piece by dual injection of an elastomer-and-thermoplastic material and of a thermoplastic material.

10. An endpiece according to claim 1, characterized in that said core (2) possesses an enlarged head that is substantially cylindrical.

11. An endpiece according to claim 1, characterized in that the central orifice of said wall (111) is formed by a cylindrical bore, while said stud (20) is substantially frustoconical in profile.

12. An endpiece according to claim 1, characterized in that the outside face of said wall (111) is set back from the top rim (11a) of said body (1) so as to define a cup.

13. An endpiece according to claim 1, characterized in that said spray nozzle is formed beneath said wall (111) by intermediate spaces situated radially outside the periphery of said wall between the inner faces of said body (1) and the outer envelope of said core (2).

* * * * *